(12) United States Patent
McGuckin, Jr. et al.

(10) Patent No.: US 9,271,727 B2
(45) Date of Patent: *Mar. 1, 2016

(54) APPARATUS AND METHOD FOR RESECTIONING GASTRO-ESOPHAGEAL TISSUE

(71) Applicant: REX MEDICAL, L.P., Radnor, PA (US)

(72) Inventors: James F. McGuckin, Jr., Radnor, PA (US); Peter W. J. Hinchliffe, Downington, PA (US)

(73) Assignee: REX MEDICAL, L.P., Radnor, PA (US)

( * ) Notice: Subject to any disclaimer, the term of this patent is extended or adjusted under 35 U.S.C. 154(b) by 384 days.

This patent is subject to a terminal disclaimer.

(21) Appl. No.: 13/856,819

(22) Filed: Apr. 4, 2013

(65) Prior Publication Data

US 2013/0228610 A1 Sep. 5, 2013

Related U.S. Application Data

(63) Continuation of application No. 11/471,126, filed on Jun. 20, 2006, now Pat. No. 8,424,741, which is a continuation of application No. 10/855,908, filed on May 27, 2004, now Pat. No. 7,090,684, which is a continuation of application No. 10/062,760, filed on Jan. 31, 2002, now Pat. No. 6,835,199.

(60) Provisional application No. 60/265,469, filed on Jan. 31, 2001.

(51) Int. Cl.
*A61B 17/068* (2006.01)
*A61B 17/072* (2006.01)
*A61B 1/273* (2006.01)
*A61B 17/00* (2006.01)
*A61B 17/29* (2006.01)

(52) U.S. Cl.
CPC ......... *A61B 17/068* (2013.01); *A61B 17/07207* (2013.01); *A61B 1/2736* (2013.01); *A61B 17/00234* (2013.01); *A61B 2017/00278* (2013.01); *A61B 2017/00827* (2013.01); *A61B 2017/07214* (2013.01); *A61B 2017/07221* (2013.01); *A61B 2017/2905* (2013.01); *A61B 2017/2923* (2013.01)

(58) Field of Classification Search
CPC ...................................................... A61B 17/072
USPC .................. 227/176.1, 179.1, 180.1; 606/139
See application file for complete search history.

(56) References Cited

U.S. PATENT DOCUMENTS 7,090,684 B2 * 8/2006 McGuckin et al. ........... 606/139
8,424,741 B2 * 4/2013 McGuckin et al. ........ 227/179.1

* cited by examiner

*Primary Examiner* — Nathaniel Chukwurah
(74) *Attorney, Agent, or Firm* — Fay Kaplun & Marcin, LLP

(57) ABSTRACT

A system for stapling tissue includes a stapling head and a control unit. The stapling head includes an endoscope receiving lumen extending therethrough and first and second jaws movable with respect to one another between a tissue receiving configuration and a tissue stapling configuration. The first jaw includes a staple firing mechanism and the second jaw includes a staple forming surface. The stapling head further includes gross and fine movement mechanisms controlling gross and fine movements, respectively, of one of the first and second jaws relative to the other of the first and second jaws. The control unit includes a first actuator controlling the gross and fine movement mechanisms and a second actuator operating the stapling mechanism.

20 Claims, 11 Drawing Sheets

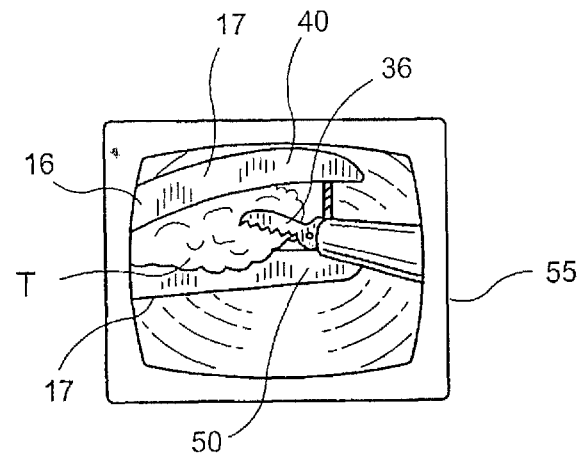
F I G. 2b
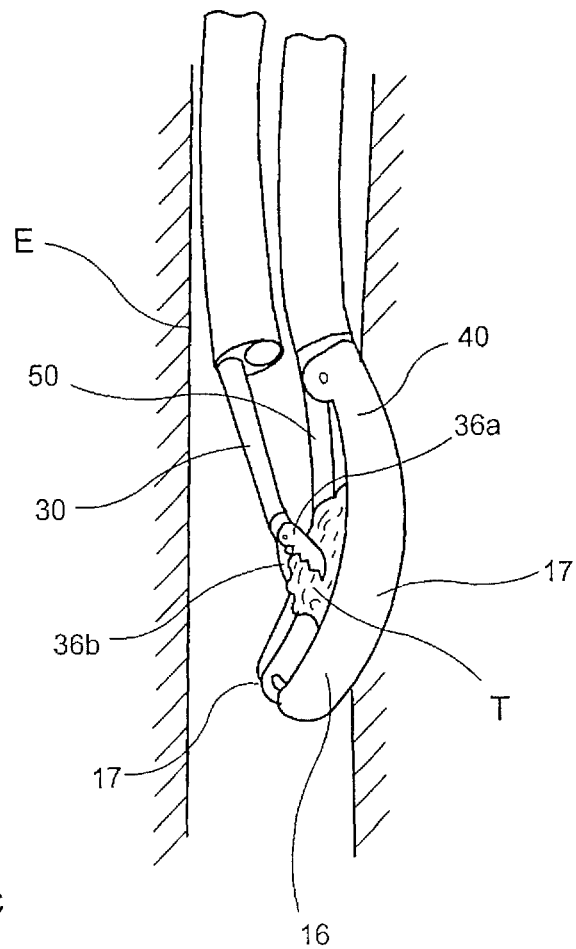
F I G. 2c

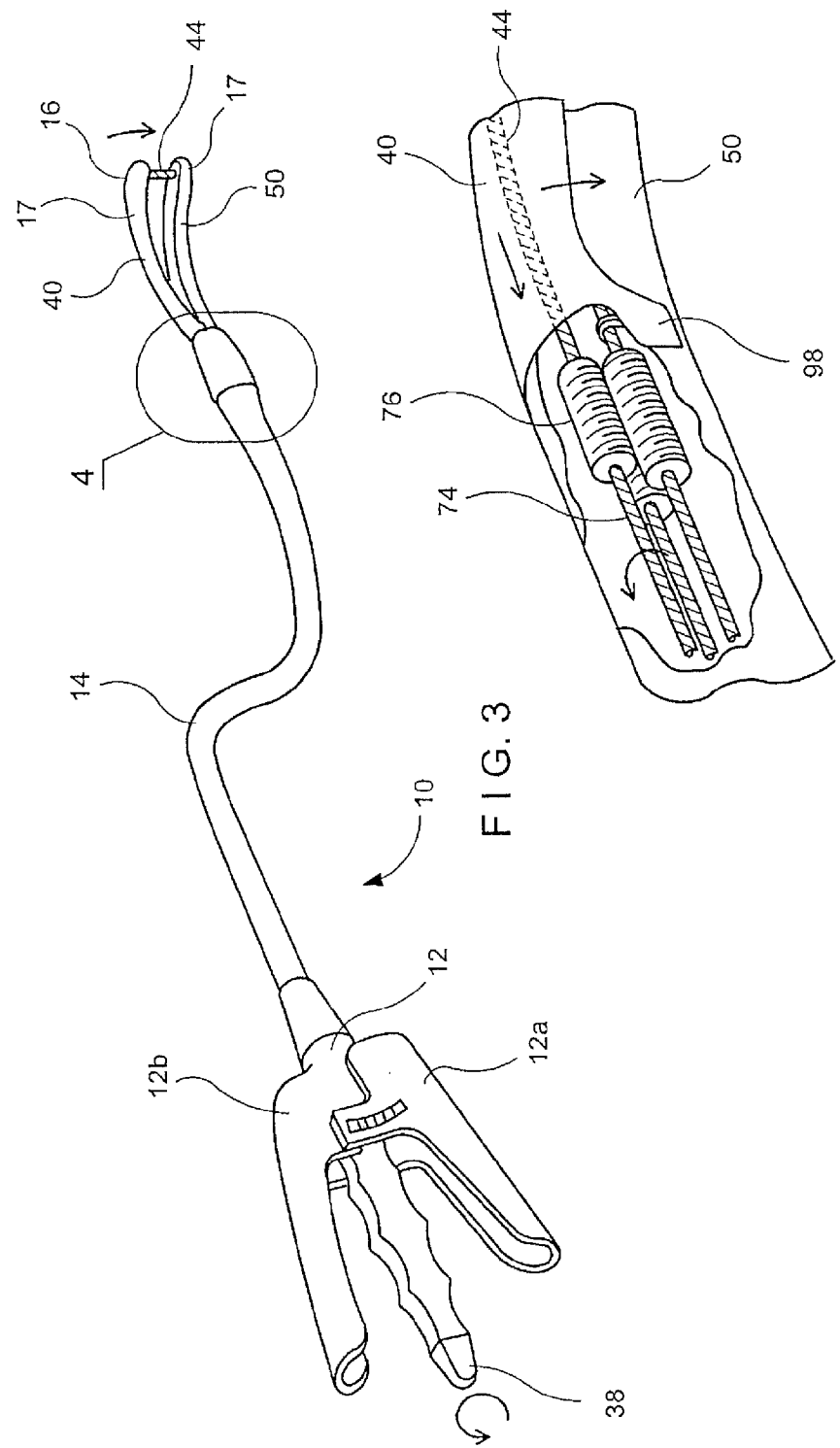

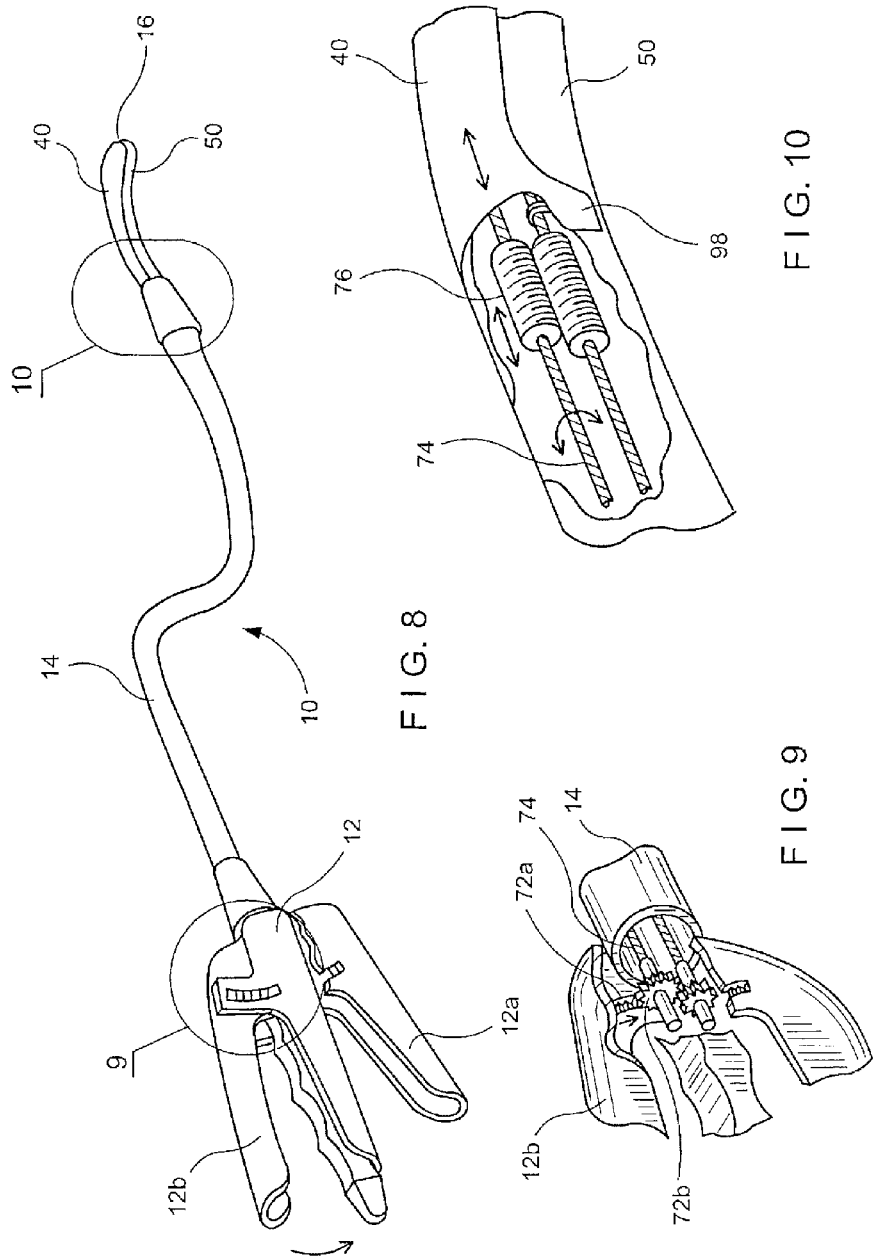

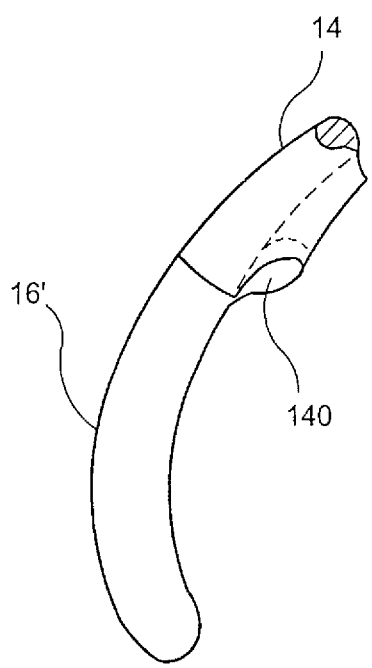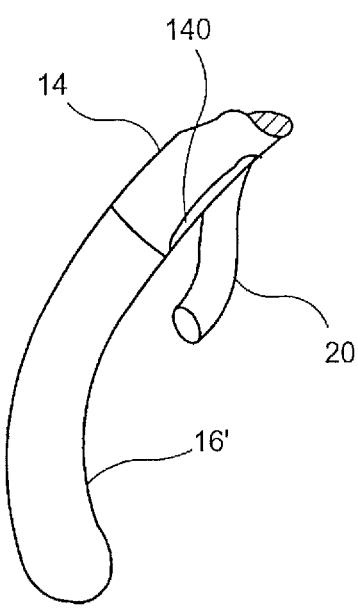
F I G. 19   F I G. 20

APPARATUS AND METHOD FOR RESECTIONING GASTRO-ESOPHAGEAL TISSUE

PRIORITY CLAIM

This application is a Continuation of U.S. patent application Ser. No. 11/471,126 filed Jun. 20, 2006, now U.S. Pat. No. 8,424,741, which is a Continuation of U.S. patent application Ser. No. 10/855,908 filed May 27, 2004, now U.S. Pat. No. 7,090,684, which is a Continuation of U.S. patent application Ser. No. 10/062,760 filed Jan. 31, 2002, now U.S. Pat. No. 6,835,199, which claims benefit of U.S. Provisional Patent Application Ser. No. 60/265,469 filed Jan. 31, 2001. The entire disclosures of these prior applications/patents are considered part of the disclosure of the accompanying application and hereby expressly incorporated by reference herein.

FIELD OF THE INVENTION

The present invention relates to endoscopic devices for performing localized resections of gastro-esophageal lesions.

BACKGROUND OF THE INVENTION

Endoscopic surgical stapling apparatus are known in the art and are utilized to provide a variety of surgical procedures. For example, U.S. Pat. No. 5,040,715 to Green, et al. discloses an endoscopic stapling device configured to be inserted through a small entrance wound in the abdominal cavity to place rows of staples in body tissue. This device has a limited range of motion in that the stapling assembly at the distal end of the instrument can only be rotated about the central axis of the instrument.

An endoscopic stapling apparatus purporting to have a greater range of motion is disclosed in U.S. Pat. No. 5,326,013 to Green et al. This device has an articulating stapling assembly mounted for pivotal movement about an axis extending transverse to the central axis of the instrument. An endoscopic stapling device designed to be inserted through a small incision in a body wall and purporting to have an increased range of motion is described in U.S. Pat. No. 5,389,098 to Tsuruta et al. A stapling assembly of this device curves away from a central axis of the instrument to a 90.degree. angle so that it can more easily reach tissue spaced from the central axis. This device incises tissue clamped within the stapling assembly and places staggered lines of staples on both sides of the incision.

SUMMARY OF THE INVENTION

The present invention is directed to a system for stapling tissue comprising a flexible endoscope and an operative head including a pair of opposed, curved tissue clamping jaws sized to pass through an esophagus, the jaws being moveable with respect to one another between an open tissue receiving configuration and a closed tissue clamping configuration, a first one of the curved jaws including a stapling mechanism and a second one of the jaws including a staple forming anvil surface, the stapling mechanism including staple slots through which staples are fired arranged in a row extending from a proximal end of the first jaw to a distal end thereof in combination with a control handle which, when the operative head is in an operative position within one of a patient's stomach and esophagus, remains outside the patient, the control handle including a first actuator for moving the jaws relative to one another and a second actuator for operating the stapling mechanism.

BRIEF DESCRIPTION OF THE DRAWINGS

FIG. 2b shows a display of the image of a stapling apparatus of the system of FIG. 1 provided to a user;

FIG. 2c shows a cross-sectional view of the patient's esophagus with the stapling apparatus of FIG. 3 in position adjacent to the target portion of tissue;

FIG. 3 shows a perspective view of the system of FIG. 1 with jaws of the stapling apparatus open;

FIG. 4 shows a partially cross-sectional view of a proximal end of the stapling apparatus of FIG. 3 showing control cables for operating the jaws configured as when the jaws are open;

FIG. 8 shows a perspective view of the system of FIG. 1 with jaws of the stapling apparatus closed with an upper actuator lever on the control handle being actuated;

FIG. 9 shows a partially cross-sectional view of a portion of the control handle of the system of FIG. 8 showing a coupling between control cables for operating the jaws and the upper actuator lever on the control handle;

FIG. 10 shows a partially cross-sectional view of a proximal end of the stapling apparatus of FIG. 5 showing control cables for operating a stapling pusher of the stapling apparatus configured as when the upper actuator lever is actuated;

FIG. 19 shows an alternate embodiment of the system according to the present invention with a lateral endoscope receiving lumen;

FIG. 20 shows the system of FIG. 19 with an endoscope received therein;

DETAILED DESCRIPTION

Figure 1:
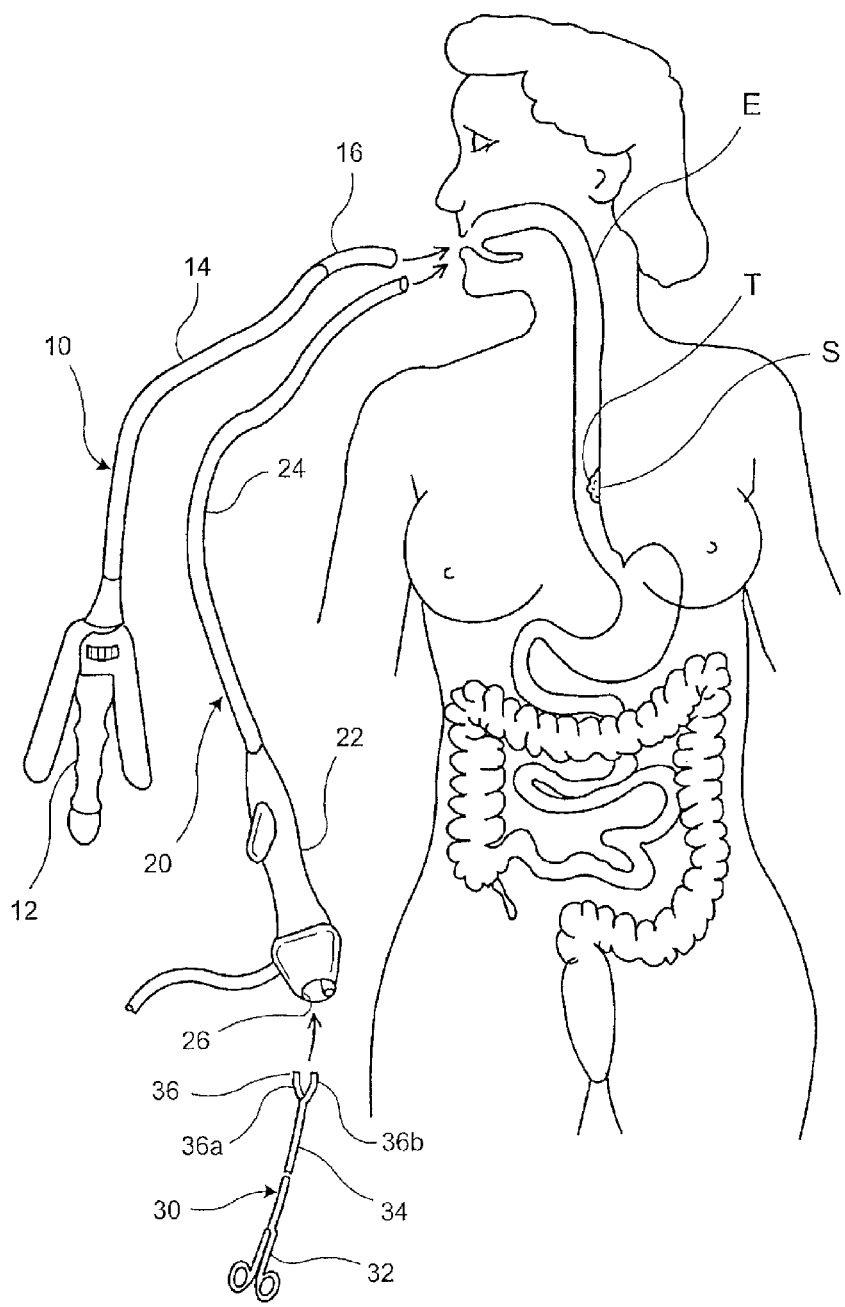
FIG. 1 shows a perspective view of a system according to an illustrative embodiment of the present invention along with a partially cross-sectional view of a patient showing a target portion of tissue to be resected.

A detailed description of illustrative embodiments of the present invention is provided in conjunction with the attached drawings. In the descriptions of the various embodiments and the corresponding drawings, like reference numerals refer to like elements.

A method and apparatus for resectioning anastomized lumenal tissue is disclosed in U.S. Pat. No. 5,868,760 to McGuckin et al., the disclosure of which is hereby incorporated by reference in its entirety. The disclosed apparatus includes a flexible tubular body and a distal operating capsule that may be inserted through either a naturally occurring body orifice or a surgical incision and guided to an operative site endoscopically or using radiologic imaging guidance. In use the target tissue is stapled, cut and captured within the operating capsule for removal from the body. The healthy tissue is thereby anastomized by surgical staples.

FIG. 1 shows a system for resecting esophageal tissue according to an illustrative embodiment of the present invention. A surgical stapling apparatus, designated generally by the reference numeral 10, is utilized in conjunction with an endoscope 20 for providing remote vision of an operative area and to assist in guiding the stapling apparatus 10 to the operative area. An endoscopic grasping device 30 extends through a lumen in the endoscope 20 for use at the surgical site as would be understood by those of skill in the art. Those skilled in the art will further understand that, while the illustrative embodiments are described in conjunction with visual observation of the operative site via the endoscope 20, these procedures may also be visualized through the use of Magnetic Resonance Imaging (MRI). In this case, components of the system and the instruments utilized therewith, such as the grasping device 30, would be constructed from non-ferrous material such as titanium, as would be understood by those of skill in the art.

As shown in FIG. 1, the stapling apparatus 10 includes a proximal handle portion 12, an elongated flexible body portion 14 extending from the handle portion 12 and a generally C-shaped stapling assembly 16 operatively associated with a distal end of the flexible body portion 14. The flexible body portion 14 and the stapling assembly 16 are preferably dimensioned and configured to traverse the natural curvature of the esophagus. As shown in FIGS. 2b and 2c and described in detail below, the stapling assembly 16 includes a pair of opposable jaws 17 defined by a staple carrying portion 40 and a staple forming portion 50. Those skilled in the art will understand that, although the jaws 17 are described herein as rotating relative to one another between the open and closed positions, that these jaws 17 may be coupled by a mechanism which allows them to move linearly with respect to one another or in any other manner so long as they move between a first position in which the jaws 17 are separated from one another to receive tissue and a second position in which the jaws 17 are clamped together to hold tissue tightly therebetween for stapling.

Furthermore, those skilled in the art will understand that the system may operate with any of a variety of commercially available medical endoscopes which may include, for example, a proximal handle portion 22, an elongated flexible body portion 24 through which one or more interior lumena extend for accommodating, for example, a fiber optic bundle or other image transmission structure, a working channel for the grasping device 30, etc. Those skilled in the art will understand that the fiber optic bundle (or other image transmitting structure) allows a user to remotely visually monitor a field of view at the distal end of the endoscope (e.g., an operative site S within the esophagus E). As would be further understood by those of skill in the art, the tissue grasping device 30 may include a handle portion 32, an elongated flexible body portion 34 and a pair of opposable jaws 36, which consists of first and second opposable jaw 36, which consists of first and second opposable jaws 36a and 36b.

Figure 2A:
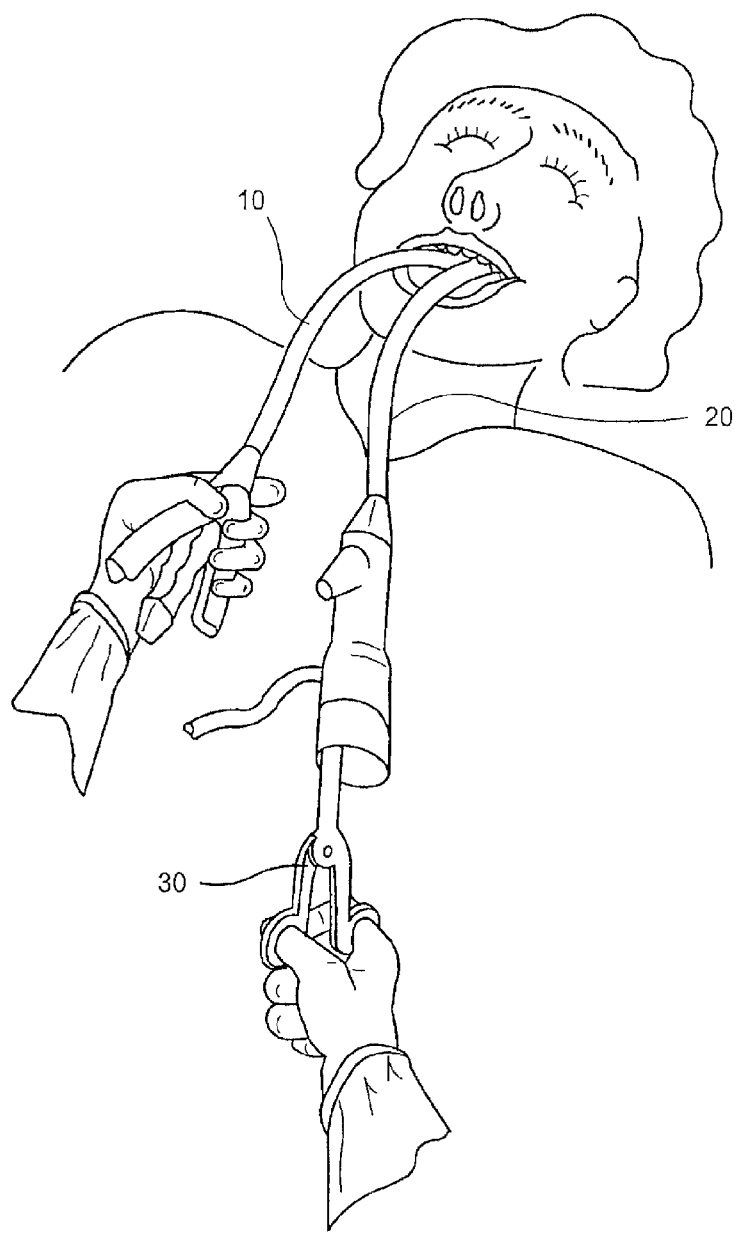
FIG. 2a shows the system of FIG. 1 inserted into the patient's body via the mouth.

In use as shown in FIGS. 2a-2c, the surgical stapling apparatus 10 and the flexible endoscope 20 are introduced into a patient's mouth and advanced into the esophagus to the operative site S under visual guidance from the endoscope 20. Once at the site S, the operator maneuvers the stapling assembly 16 into a desired position relative to the tissue to be resected. Those skilled in the art will understand that the stapling assembly 16 may be coupled to the handle portion 22 by a cable steering system (not shown) substantially as included in commercially available endoscopes to allow the remote maneuvering and positioning of the stapling assembly 16. The jaws 17 of the stapling assembly 16 are then opened to a tissue receiving position as shown in FIG. 3 and the grasping device 30 is advanced from the distal end of the endoscope 20. The jaws 36a and 36b are rotated away from one another by manipulation of the grasper handle portion 32 and the tissue T to be resected is grasped by closing the jaws 36a, 36b. The grasping device 30 is then withdrawn into the working channel of the endoscope 20 to pull the tissue T into position between the jaws 17 of the stapling assembly 16 and the jaws 17 are closed to clamp the tissue T in place between the staple carrying portion 40 and the staple forming portion 50. Those skilled in the art will understand that the tissue T is preferably drawn between the jaws 17 so that a margin of healthy tissue is positioned between the staple carrying portion 40 and the staple forming portion 50 to ensure that all of the diseased or damaged tissue T is removed. Those skilled in the art will understand that this may be visually confirmed through the use of a vision system 55 of the endoscope as shown in FIG. 2b.

Figure 12:
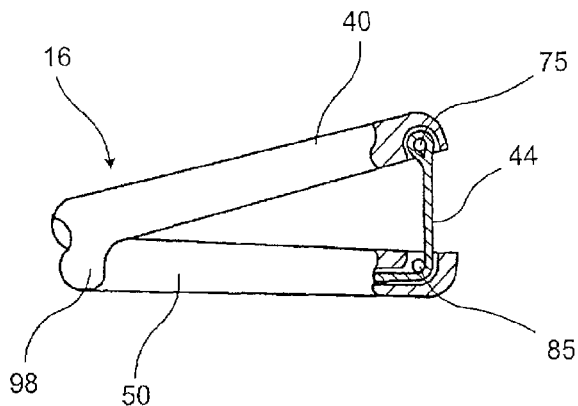
FIG. 12 shows a partially cross-sectional view of the stapling assembly of the system of FIG. 1 illustrating a mechanism for grossly approximating the jaws of the stapling assembly.
Figure 16:
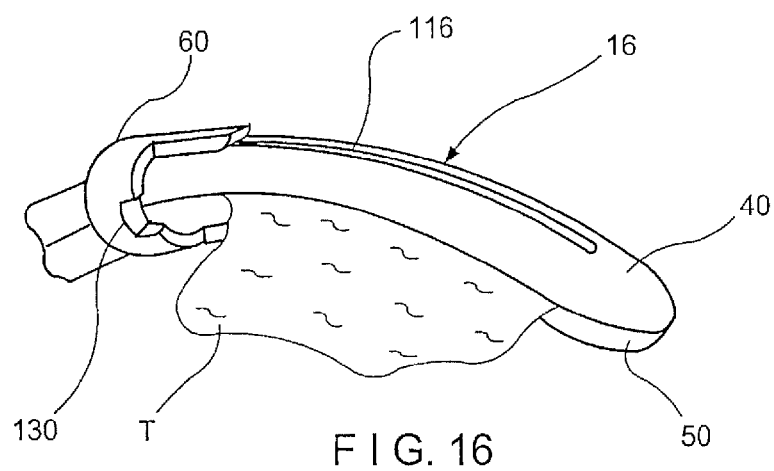
FIG. 16 shows a perspective view of the stapling assembly with a C-shaped clamp member thereof in an initial position.
Figure 17:
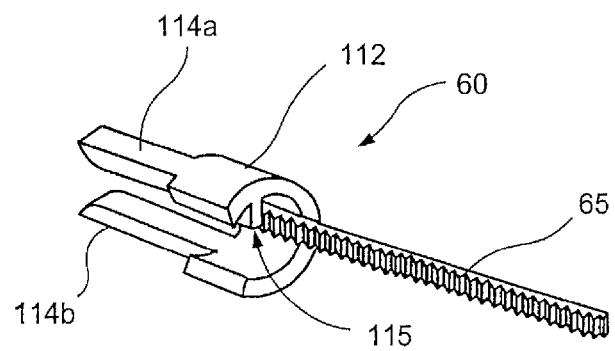
FIG. 17 shows a perspective view of the C-shaped clamp member of FIG. 16 rotated 180.degree. removed from the jaws.
Figure 18:
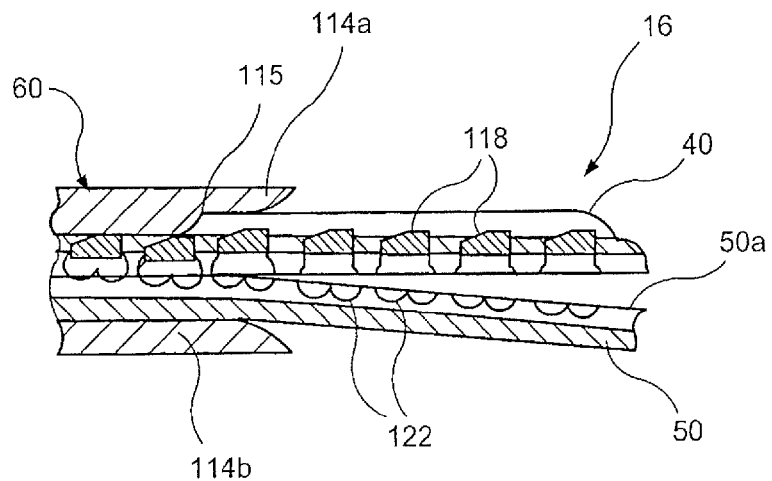
FIG. 18 shows a cross-sectional view of the stapling assembly with the C-shaped clamp member in a partially advanced position.

As shown in FIG. 2c, once the tissue T has been properly positioned between the jaws 17, the jaws 17 are grossly approximated and are then finely approximated using a translating clamping member 60, illustrated in detail in FIGS. 16-18. As shown in FIGS. 3, 4 and 12, an illustrative embodiment of the system according to the present invention includes an actuation cable 44 to facilitate gross approximation of the jaws 17 via actuation of an actuator knob 38. The actuation cable 44 may be secured to the one of the jaws 17 including, for example, the staple carrying portion 40 by a member 75, which may, for example be a spindle, capstan or other member around which cable 44 loops. The cable 44 is operatively coupled to the other jaw 17 including the staple forming portion 50 by a member 85, which is substantially similar to the member 75 and around which the cable 44 passes to change direction to generate the clamping force to draw the jaws 17 together. Furthermore, an overhanging flange 98 at a proximal end of the staple carrying portion 40 acts as a tissue shield preventing the target tissue T from entering into the joint between the jaws 17.

Figure 5:
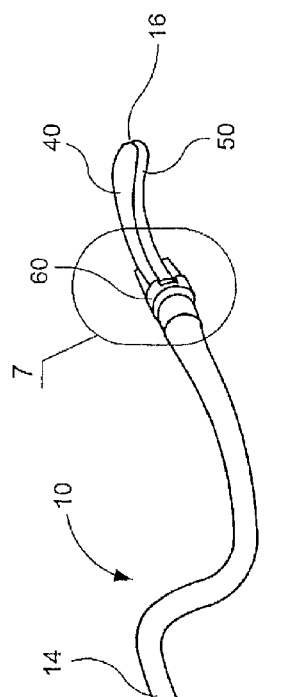
FIG. 5 shows a perspective view of the system of FIG. 1 with jaws of the stapling apparatus closed with a lower actuator lever on a control handle being actuated.
Figure 7:
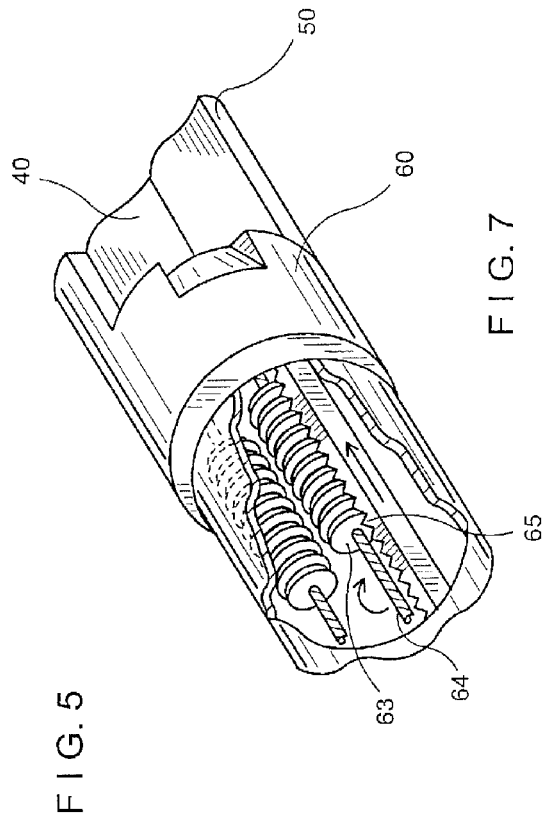
FIG. 7 shows a partially cross-sectional view of a proximal end of the stapling apparatus of FIG. 5 showing control cables for operating a stapling pusher of the stapling apparatus configured as when the lower actuator lever is actuated.
Figure 6:
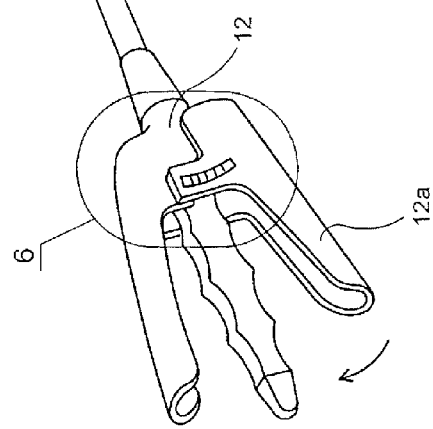
FIG. 6 shows a partially cross-sectional view of the control handle of the system of FIG. 5 showing a coupling between control cables for operating the jaws and the lower actuator lever on the control handle.

As shown in FIGS. 3-7, to actuate the clamping member 60 to finely approximate the jaws 17, the lower clamping handle 12a is actuated in the direction of the arrow in FIG. 5 to cause the integral gear rack 62a to turn pinion gear 62b which rotates elongated drive cable 64. As shown in FIG. 7, the drive cable 64 is coupled to a drive screw 63 interacting with a geared surface 65 so that rotation of the drive cable 64 rotates the drive screw 63 moving the clamping member 60 distally as shown in FIG. 18. This finely approximates the jaws 17 of the stapling assembly 16 whereby a tissue contacting surface of the staple carrying portion 40 and a tissue contacting surface of the staple forming portion 50 are brought into cooperative alignment, tightly clamping the tissue therebetween. Those skilled in the art will understand that alternative sources of power (e.g., electrical, hydraulic, pneumatic, etc.) may be applied to drive the jaws 17 and to drive all other mechanisms of the stapling assembly 16.

As shown in FIG. 8, once the jaws 17 have been brought into cooperative alignment with one another, the stapling assembly 16 may be actuated to fire staples through the clamped tissue while simultaneously cutting away the tissue T from the stapled and anastamized tissue. The user actuates the stapling assembly 16 to drive staples through the margin of healthy tissue in one or more arcuate bands located radially outward of a line of tissue cutting. Alternatively, those skilled in the art will understand that the stapling operation may be separated from the tissue cutting operation so that no tissue is cut until the entire stapling operation has been successfully concluded.

Specifically, as shown in FIGS. 8-10, the operator drives an I-beam member 70 through the stapling assembly 16 by operating the clamping handle 12b in the direction of the arrow in FIG. 8, causing gear rack 72a to rotate pinion gear 72b which rotates a staple driving drive cable 74 as shown in FIG. 9. The drive cable extends through the flexible body portion 14 to a linear drive screw 76 which drives a flexible pusher 80 coupled to the I-beam member 70 as shown in FIG. 10.

Figure 11:
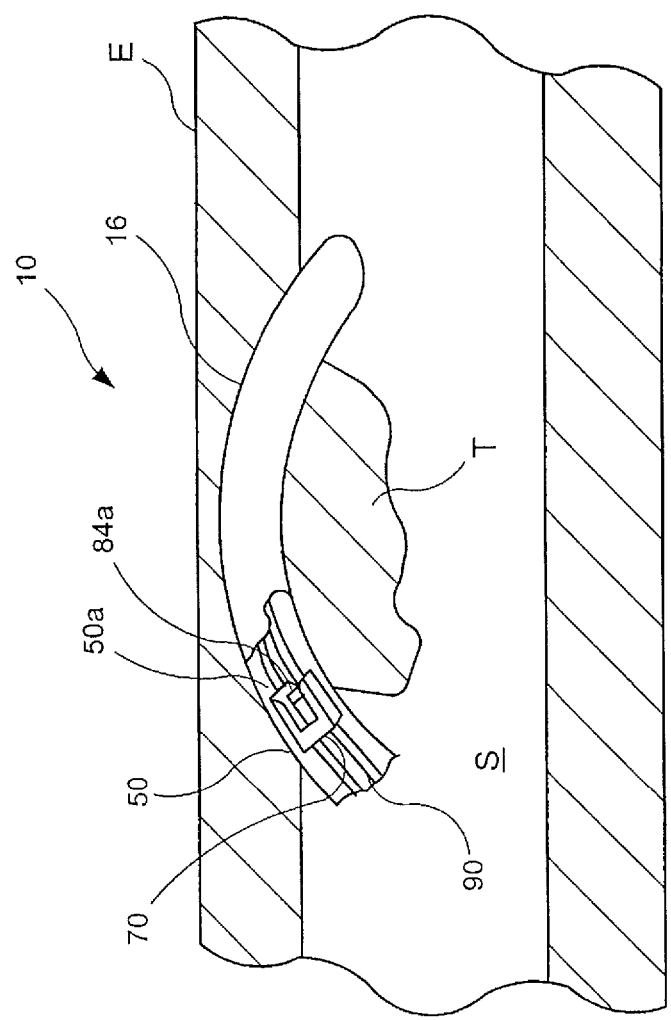
FIG. 11 shows a partially cross-sectional view of a stapling assembly of the system of FIG. 1 grasping esophageal tissue.

As shown in FIGS. 11, 13, 14 and 15, the I-beam member 70 includes upper and lower beam portions 82a, 82b, respectively, connected by a central web portion 84. A leading edge 84a of the central web portion 84 may preferably define a cutting blade for incising tissue as the I-beam member 70 is moved distally as described below. As shown in FIG. 11, an arcuate channel 90 within which the central web portion 84 travels, is defined in the opposing jaws 17 radially inward of the arcuate lines of staple carrying slots (not shown). Those skilled in the art will understand that the staple slots may be arranged in any number of rows, for example, from one to five such rows may be included and the slots of these rows may be staggered so that to ensure that the opening created by the resection is completely sealed.

Figure 13:
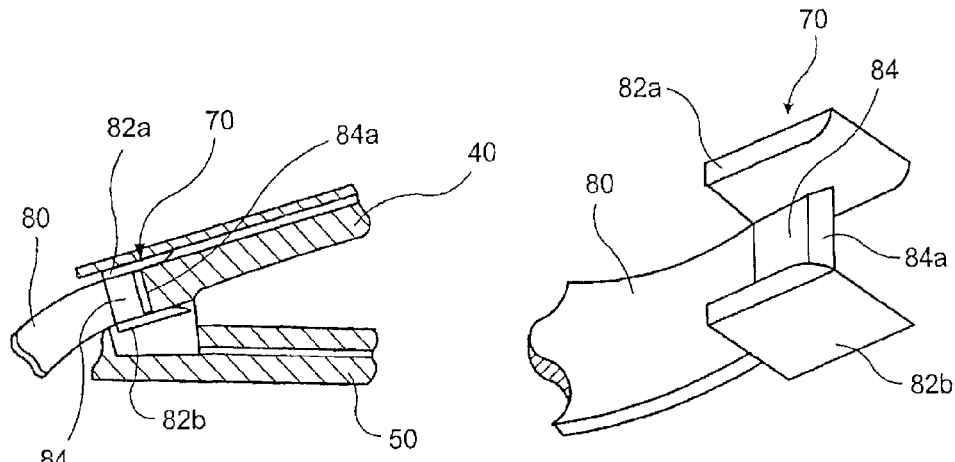
FIG. 13 shows a partially cross-sectional view of the stapling assembly illustrating a mechanism for finely approximating the jaws in an initial position.
Figure 14:
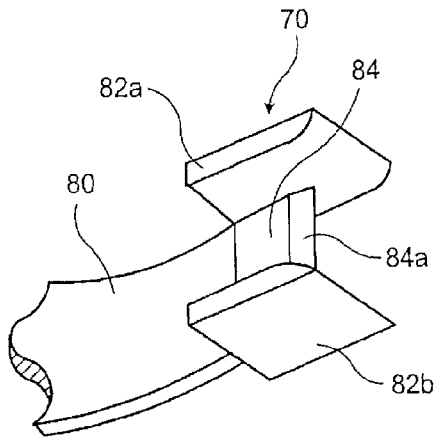
FIG. 14 shows a perspective view of an I-beam member of the fine approximation mechanism of FIG. 13.
Figure 15:
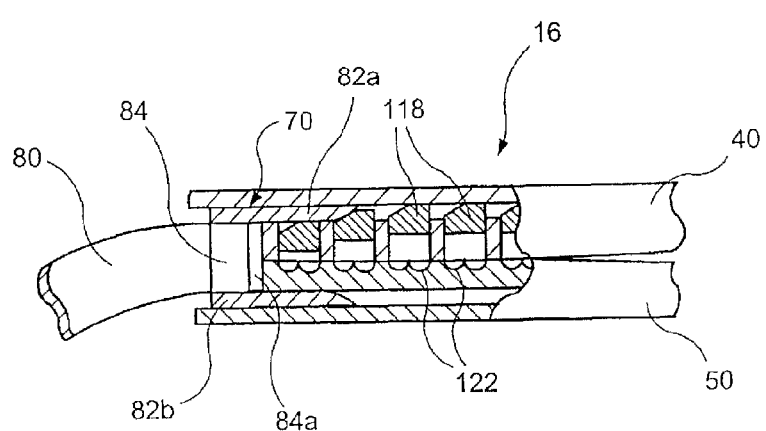
FIG. 15 shows a partially cross-sectional view of the stapling assembly with the fine approximation mechanism in a partially advanced position.

As described above, actuation of the lower handle 12a causes the C-shaped clamp member 60 to move along an arc the length of the curved stapling assembly 16 to finely approximate the jaws 17 toward one another. As shown in FIGS. 13, 14 and 15, the clamp member 60 includes a body portion 112 from which depend upper and lower clamping beams 114a and 114b, respectively, for urging the jaws 17 toward one another.

In addition, as shown in FIGS. 16 and 17, in one embodiment of the invention, the body 112 includes a radially depending driving stem 115 having a sloped leading edge configured to extend through an arcuate slot 116 formed in the staple carrying portion 40 for sequentially contacting each of a plurality of staple pushers 118. The staple pushers 118 are positioned so that, when contacted by the driving stem 115, each staple pusher 118 is driven through a corresponding one of the staple slots to drive a staple housed therein from the slot out of the staple carrying portion 40, through both thicknesses of the folded portion of tissue clamped between the jaws 17 and against the staple forming surface 50a of the staple forming portion 50 to couple the two thicknesses of tissue to one another. In this embodiment, the clamping member 60 further includes an integral cutting blade 130 for forming an arcuate incision substantially concentric with and radially within an inner one of the arcs of staple slots. Furthermore, the cutting blade 130 is preferably positioned so that it trails the leading edge 115 so that tissue is stapled before it is cut.

As shown in FIG. 15, according to a further embodiment of the invention, actuation of the upper actuation handle 12b causes the I-beam member 70 to move through the stapling assembly 16 to sequentially fire arcuate rows of staples while simultaneously cutting tissue away from the esophagus radially within the rows of staples. When the I-beam member 70 is driven by the pusher 80, the sloped leading edge of the upper beam portion 82a contacts sequentially each of a plurality of staple pushers 118 to drive them through their respective staple slots to drive the staples housed therein from each slot out of the staple carrying portion 40, through both thicknesses of the folded portion of tissue clamped between the jaws 17 and into the staple forming pockets 122 formed in the staple forming surface 50a of the staple forming portion 50 to couple the two thicknesses of tissue to one another. As the leading edge 84a of the central web portion 84 is proximal to the sloped leading edge, the incision trails the stapling action so that only tissue within the arc that has previously been stapled is severed.

As shown in FIGS. 19 and 20, according to a further embodiment of the invention, a stapling assembly 16' according to the present invention may include an endoscope receiving lumen 140 through which the endoscope 20 may be slidably inserted. This allows an operator to use to steering and vision capability of the endoscope 20 to locate the operative site S. Once the distal end of the endoscope 20 is positioned adjacent to the site S, the stapling assembly 16' may be slid along the endoscope 20 to the operative site S and the steering capability of the distal end of the endoscope 20 may be employed to achieve a desired position and orientation of the stapling assembly 16' relative to the tissue T. Other than the endoscope receiving lumen 140, the construction of the rest of the system of FIGS. 19 and 20 may be substantially in accord with that of any of the previously described embodiments.

Figure 21:
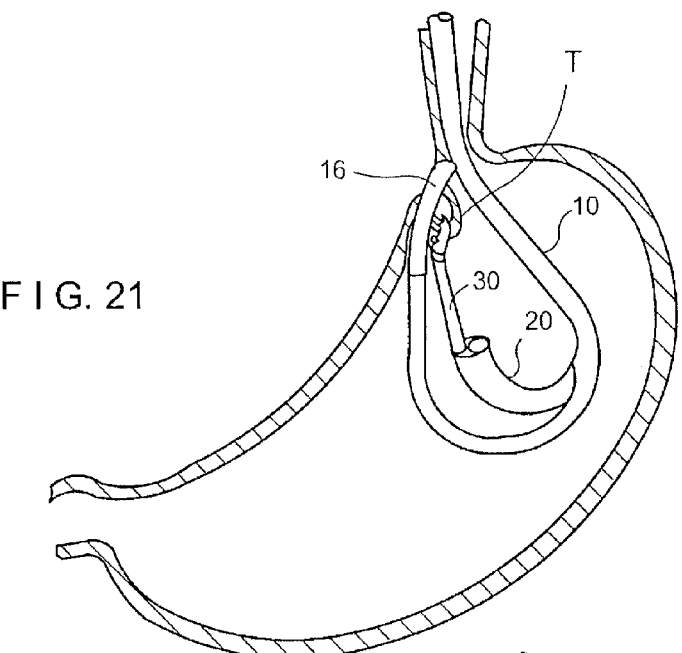
FIG. 21 shows a system in accord with the present invention positioned within the stomach to perform a procedure for the treatment of reflux.
Figure 22:
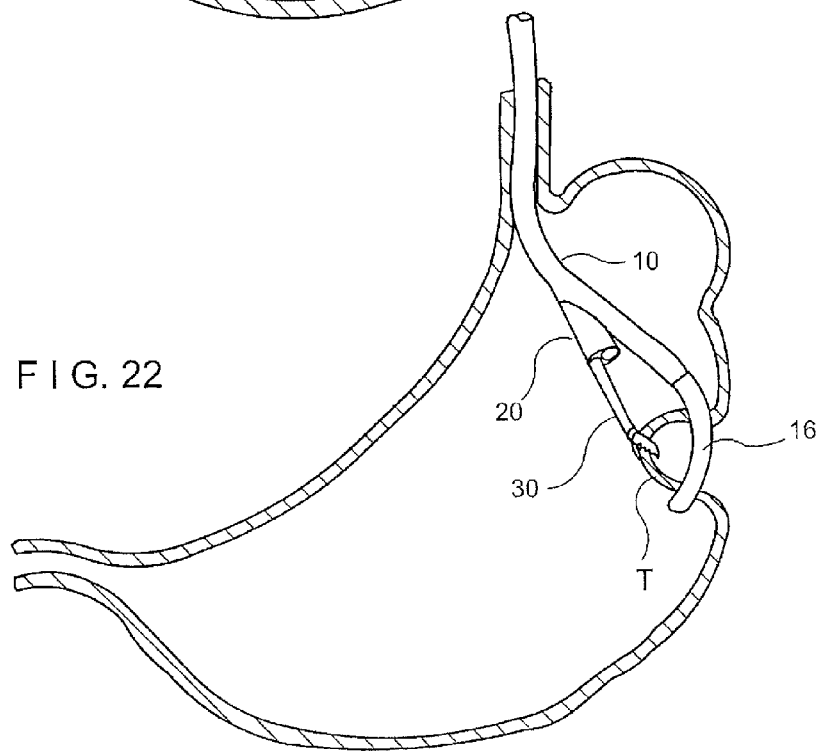
FIG. 22 shows a system in accord with the present invention positioned within the stomach to perform a stomach reduction procedure.

Furthermore, as shown in FIGS. 21 and 22, the system according to the present invention may also be used to perform resections within the stomach. For example, the stapling apparatus 10 may be used to correct gastro-esophageal reflux ("GERD") or to perform a stomach reduction procedure. Specifically, as shown in FIG. 21, a system according to the invention may be inserted through the esophagus into a patient's stomach and the operator may position the jaws 17 under visual control via the endoscope 20 adjacent to a junction between the esophagus and the stomach. The operator then uses the steering capability of the endoscope 20, received within the endoscope lumen 140 to direct the jaws 17 toward a portion of stomach tissue to be fastened to the esophagus. Specifically, the operator grasps a portion of the stomach using the grasping device 30 and urges the tissue T toward the esophagus to create a fold of tissue with an outside surface of the stomach tissue adjacent to or in contact with an outer surface of the esophagus. This fold is then clamped by the jaws 17 and stapled together to reduce the diameter of the opening from the esophagus to the stomach. The tissue radially within the stapled tissue is then resected.

Similarly as shown in FIG. 22, to perform a stomach reduction, an operator inserts a system according to the present invention into the stomach via the esophagus as described above in regard to FIG. 21 and locates a portion of tissue to be folded over on itself to reduce the size of the stomach. This tissue T is grasped by the grasping device 30 and drawn between the jaws 17 which clamp the tissue T together folded onto itself and staples the fold together. Those skilled in the art will understand that, for a stomach reduction procedure, the folded tissue radially within the staples may, if desired, be left in place without resection so that the operation may be reversed at a later date. Thus, for such a stomach reduction procedure where the folded, stapled tissue will be left in place within the stomach, the stapling apparatus 10 need not include a tissue cutting mechanism. Rather, the stapling apparatus 10 need only include structure for approximating the jaws 17 and for driving staples through the gripped fold of tissue. In this case, the C-shaped clamp member 60 would be constructed without the cutting blade 130.

The above described embodiments are for purposes of illustration only and the various modifications of these embodiments which will be apparent are considered to be within the scope of the teachings of this invention which is to be limited only by the claims appended hereto.

What is claimed is:

1. A method for stapling tissue, comprising the steps of:
   inserting into a body a tissue resectioning device including a stapling head having a first jaw including a staple firing mechanism and a second jaw including a staple forming surface;
   drawing a fold of tissue between the first and second jaws;
   actuating a gross movement mechanism to move the first and second jaws toward a desired tissue stapling configuration compressing the fold between the first and second jaws;
   actuating a fine movement mechanism in the stapling head to finely adjust a position of the first and second jaws to the desired tissue stapling configuration; and
   actuating the staple firing mechanism to drive staples through the fold and against the staple forming surface.

2. The method according to claim 1, wherein the step of actuating the fine movement mechanism includes sliding a clamp distally over the first and second jaws.

3. The method according to claim 2, wherein the clamp is substantially C-shaped.

4. The method according to claim 1, wherein the step of actuating the staple firing mechanism includes driving staples from stapling slots arranged in a row in the first jaw to form a row of staples in the fold.

5. The method according to claim 4, further comprising cutting tissue radially within the row of staples.

6. The method according to claim 5, wherein the driving step includes moving a staple pusher in the first jaw distally to drive staples in the stapling slots successively through the fold and against the staple forming surface of the second jaw.

7. The method according to claim 1, further comprising inserting an endoscope into the body.

8. The method according to claim 7, wherein the step of inserting the tissue resectioning device includes sliding the stapling head along the endoscope into the body.

9. A method for reducing a volume of a stomach, comprising:
   inserting an endoscope into the stomach;
   sliding a tissue resectioning device along the endoscope into the stomach, the tissue resectioning device including a stapling head having a first jaw including a staple firing mechanism and a second jaw including a staple forming surface, the stapling head further including a tissue cutting mechanism;
   drawing a fold of tissue between the first and second jaws;
   actuating a gross movement mechanism in the stapling head to move the first and second jaws toward a desired tissue stapling configuration so that the fold is compressed between the first and second jaws to the desired tissue stapling configuration;
   actuating a fine movement mechanism in the stapling head to finely adjust a position of the first and second jaws;
   actuating the staple firing mechanism to drive staples through the fold and against the staple forming surface; and
   actuating the tissue cutting mechanism to resect a portion of the fold.

10. The method according to claim 9, wherein the step of actuating the fine movement mechanism includes sliding distally a clamp over the first and second jaws.

11. The method according to claim 10, wherein the clamp is substantially C-shaped.

12. The method according to claim 11, wherein the step of actuating the staple firing mechanism includes driving staples from stapling slots arranged in a row in the first jaw to form a row of staples in the fold.

13. The method according to claim 12, further comprising cutting tissue radially within the row of staples.

14. The method according to claim 13, wherein the driving step includes moving a staple pusher in the first jaw distally to drive staples in the stapling slots successively through the fold and against the staple forming surface of the second jaw.

15. A system for stapling tissue, comprising:
   a stapling head including an endoscope receiving lumen extending therethrough and first and second jaws movable with respect to one another between a tissue receiving configuration and a tissue stapling configuration, the first jaw including a staple firing mechanism and the second jaw including a staple forming surface, the stapling head further including gross and fine movement mechanisms controlling gross and fine movements, respectively, of one of the first and second jaws relative to the other of the first and second jaws; and
   a control unit including a first actuator controlling the gross and fine movement mechanisms and a second actuator operating the stapling mechanism.

16. The system according to claim 15, further comprising a flexible endoscope sized and shaped to be slidably received within the endoscope receiving lumen such that the stapling head is slidable over the endoscope to a target tissue within the body.

17. The system according to claim 15, wherein the fine movement mechanism includes a clamp received around the first and second jaws, wherein the first actuator controls proximal and distal movement of the clamp for controlling fine movement of the first and second jaws.

18. The system according to claim 17, wherein the clamp is substantially C-shaped.

19. The system according to claim 15, wherein the gross movement mechanism includes a cable fixed at a first end to the first jaw, threaded around a spindle in the second jaw and fixed at a second end to the first actuator.

20. The system according to claim 15, further comprising a tissue cutting mechanism cutting tissue.

* * * * *